US012773136B2

(12) United States Patent
Petcavich

(10) Patent No.: US 12,773,136 B2
(45) Date of Patent: Oct. 27, 2026

(54) WEARABLE WIRELESS NON-INVASIVE BLOOD GLUCOSE MEASUREMENT SYSTEM

(71) Applicant: Robert John Petcavich, Montgomery, TX (US)

(72) Inventor: Robert John Petcavich, Montgomery, TX (US)

(73) Assignee: Robert John Petcavich, Montgomery, TX (US)

( * ) Notice: Subject to any disclaimer, the term of this patent is extended or adjusted under 35 U.S.C. 154(b) by 468 days.

(21) Appl. No.: 18/139,880

(22) Filed: Apr. 26, 2023

(65) Prior Publication Data

US 2023/0255519 A1 Aug. 17, 2023

Related U.S. Application Data

(63) Continuation-in-part of application No. 17/199,425, filed on Mar. 11, 2021, now abandoned.

(60) Provisional application No. 62/987,910, filed on Mar. 11, 2020.

(51) Int. Cl.
*A61B 5/1455* (2006.01)
*A61B 5/00* (2006.01)
*A61B 5/145* (2006.01)

(52) U.S. Cl.
CPC ...... *A61B 5/14532* (2013.01); *A61B 5/14551* (2013.01); *A61B 5/681* (2013.01)

(58) Field of Classification Search
CPC .................................................. A61B 5/14532
See application file for complete search history.

(56) References Cited

U.S. PATENT DOCUMENTS

2003/0060693 A1* 3/2003 Monfre ................ A61B 5/1455 600/322
2019/0192086 A1* 6/2019 Menon ............... A61B 5/14557

* cited by examiner

*Primary Examiner* — Marjan Fardanesh
(74) *Attorney, Agent, or Firm* — Feeney IP Law; Alan F. Feeney; Logan Faucher

(57) ABSTRACT

The present invention discloses a wearable, wireless, non-invasive blood glucose measurement system comprising an infrared LED-enabled wireless ring interfaced with machine learning software wherein the ring outputs data from the wearer used to determine the blood glucose concentrations of the wearer in real time. The blood glucose data analytics can be subsequently sent to, and displayed on, a smart mobile device, such as an iPhone®, or distributed over a cloud network.

12 Claims, 3 Drawing Sheets

WEARABLE WIRELESS NON-INVASIVE BLOOD GLUCOSE MEASUREMENT SYSTEM

CROSS-REFERENCE TO RELATED APPLICATIONS

This application is a continuation-in-part of U.S. application Ser. No. 17/199,425 filed on Mar. 11, 2021 (now abandoned) that is a continuation under 35 U.S.C. § 371 of International Application No. PCT/US2021/022015 filed on Mar. 11, 2021 that claims priority to and the benefit of U.S. Provisional Application No. 62/987,910 filed on Mar. 11, 2020. The entire contents of each are incorporated herein by reference.

BACKGROUND OF THE INVENTION

The application relates generally to a wearable non-invasive blood glucose measurement system and a method to determine blood glucose concentrations in real time.

Diabetes is a metabolic disorder in which blood glucose fluctuates from its normal range (90-140 mg/dl). This disorder can occur when the pancreas, which normally releases insulin to help the body store and use the sugar and fat from ingested food, produces very little or no insulin. Diabetes can also be a result of the body's poor internal response to insulin.

Insulin is a hormone produced in body to regulate blood glucose level naturally. Under some pathological failure, the human body is not able to produce insulin or body cells become unable to use insulin.

Poor management of diabetes can lead to serious health problems such as cardiovascular diseases, damage of blood vessels, stroke, blindness, chronic kidney failure, nervous system diseases, amputation of foot due to ulceration and early death. The number of diabetic people is increasing across the world due to population growth, unhealthy diet, obesity and lack of physical activity. According to International Diabetes Federation (IDF), 382 million people suffered from diabetes in 2013, an alarming figure which is set to reach 592 million persons by 2035. In India, about 65 million people suffer from diabetes making it the 'Diabetes Capital' of the world. China, India and the United States are among the top three countries suffering from diabetes. According to world health organization (WHO), every year 35 million people die because of diabetes.

Currently, none of the available methods can cure diabetes completely. Occurrence of complications can be prevented by keeping blood glucose levels within the normal range. Regular glucose monitoring, diet plan, insulin shots and oral medications are the foundation of diabetes treatment. Regular blood glucose monitoring is the key step in efficient management of diabetes to control blood glucose.

Most of commercially available glucose measurement devices are invasive. Diabetic patients need to monitor their blood glucose two to three times a day. The invasive methods are painful, have high recurring cost and pose a danger of spreading infectious diseases. Non-invasive methods are more desirable and excellent alternatives to these devices. Enhancing glucose measurement techniques to allow easy and continuous monitoring has received a lot of attention from both academic and industrial researchers over the past three decades.

Non-invasive glucose monitoring could make millions of people more relaxed and comfortable about blood glucose testing. Thus, it is necessary to develop a non-invasive blood glucose method which can provide painless, convenient and cost-effective glucose monitoring to diabetic patients. Non-invasive monitoring system will be a major breakthrough in the area of treating diabetes patients. Various optical non-invasive techniques have been explored for development of glucose measurement system. Optical methods are one of the painless and promising methods that can be used for non-invasive blood glucose measurement.

Near-infrared (NIR) is one of the most widely explored optical techniques because of its high penetration in skin. This technique has been applied on various body parts: finger, palm, arm, forearm, earlobe, check etc. Maruo et al., designed the fiber optical probe to get spectra of forearms of type 1 diabetic individuals (Maruo K et al., (2003), Appl Spectrosc, 57(10):1236-44), the contents of which is incorporated herein in its entirety, as well as a noninvasive blood glucose assay using a newly developed near-infrared system (Mauro K et al., (2003), IEEE J Sel Top Quant, 9(2):322-30), the contents of which is incorporated herein in its entirety. The authors have reported that the results have good correlation between the predicted and reference glucose values at 1600 nm. However, to date no one has solved the problem of a noninvasive method to monitor blood glucose levels in real time.

The problem is solved by the present invention by creating a novel system of a small wearable Infrared LED enabled device that can be worn 24 hours a day, 7 days a week (24/7) and machine learning algorithms can be employed to interpret and calculate photoplethysmography data and determine blood glucose levels (BGL).

BRIEF SUMMARY OF THE INVENTION

The present invention is directed to a wearable wireless non-invasive blood glucose measurement system that is comprised of an infrared LED-enabled wireless ring and machine learning software interfaced with the ring data output to determine blood glucose concentrations in real time. The blood glucose data analytics can be subsequently sent to and displayed on a smart mobile device or distributed over a cloud network.

Another embodiment of this invention comprises of means to provide BGL's in real time to mobile devices and the internet cloud for distribution and data storage.

Yet another embodiment of this invention comprises of a device selected from a group consisting of, but not limited to, watch, wristband, implantable radio-frequency identification (RFID) devices, headphones, headbands, earrings and combinations thereof.

Figure 1:
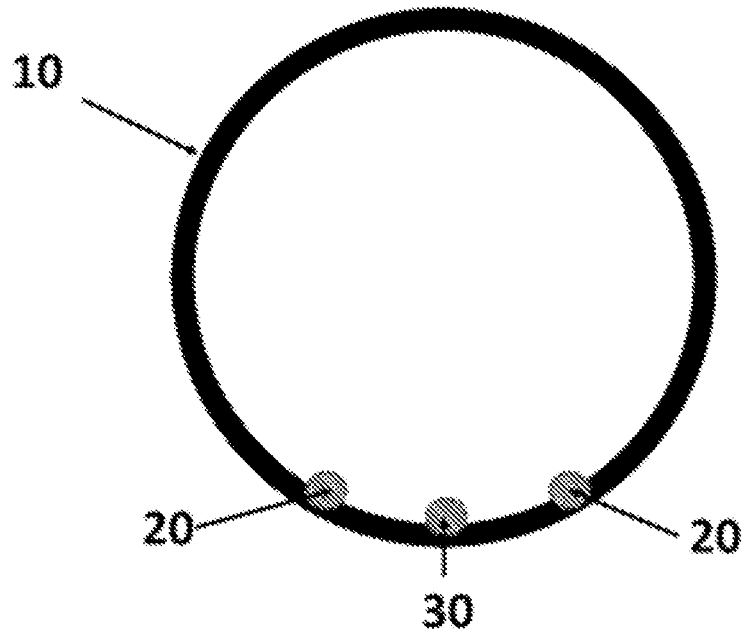
FIG. 1, shows a cross sectional view of a wearable wireless ring device of the present invention.

The renderings and images are included for illustrative and interpretive purposes relative to specific embodiments and applications and should not be construed as the sole positioning, configurations, or singular use of the present invention. These embodiments are described in sufficient detail to enable those skilled in the art to practice the invention. Other embodiments may be utilized, and structural and logical changes may be made, without departing from the scope of the present invention.

In addition, the materials, methods, and examples are illustrative only, and are not intended to be limiting. In the following detailed description, numerous specific details are provided, such as the identification of various system components, to provide an understanding of embodiments of the invention. One skilled in the art will recognize, however, that embodiments of the invention can be practiced without one or more of the specific details, or with other methods, components, materials, etc. In still other instances, well-known structures, materials, or operations are not shown or described in detail to avoid obscuring aspects of various embodiments of the invention.

DETAILED DESCRIPTION OF THE INVENTION

Definitions

The following terms are defined to aid the reader in fully understanding the operation, function, and utility of the present invention.

"Non-invasive" as used herein, refers to a method that does not require the introduction of instruments into the body.

"Measurement" as used herein, refers to an action of measuring something.

"System" as used herein, refers to a structure or apparatus.

"Comprises," "comprising," "includes," "including," "has," "having," or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus.

"And/or" refers to the possibility that both items or one or the other are claimed. For instance, reference herein to A and/or B refers to the possibility of only A, only B, or both A and B.

"A" or "an" are employed to describe elements and components of the invention. This is done merely for convenience and to give a general sense of the invention. This description should be read to include one or at least one and the singular also includes the plural unless it is obvious that it is meant otherwise.

"One embodiment" or "an embodiment" means that a particular feature, structure, or characteristic described in connection with the embodiment is included in at least one embodiment of the present invention. Thus, the appearance of the phrases "in one embodiment' or "in an embodiment in various places throughout this specification are not necessarily all referring to the same embodiment. Furthermore, the particular features, structures, or characteristics may be combined in any Suitable manner in one or more embodiments.

Reference throughout this specification to "wearable non-invasive blood glucose measurement system" is used. One ordinarily skilled in the art will recognize that embodiments of the invention should not be limited to these terms and that the terms are used as a general term for any device specifically made to hold internal contents.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, Suitable methods and materials are described below.

The Device

The present invention is intended to be a wearable wireless noninvasive system whereby blood glucose levels (BGL) can be calculated from photoplethysmography (PPG) measurements derived from the vessels. More particularly, the invention is intended to allow for real time measurements of blood glucose levels by the use of an Infrared Light Emitting Diode (IR LED) enabled ring device and machine learning algorithms. The claimed invention comprises a non-invasive blood glucose measuring device, consisting of an ultrasonic transducer for measuring the baseline glucose concentration of a patient, a laser diode light source for transmitting light energy pulses into a body tissue of the patient, and a microcontroller wherein the ultrasonic transducer detects vibration of the body tissue and generates an acoustic signal that is transmitted to a microcontroller, and wherein the concentration of the blood glucose is measured using at least one algorithm that determines the difference between the baseline and final blood glucose concentration levels. Generally, the invention is directed to a method for non-invasive measuring of blood glucose concentration levels in a patient, comprising the steps of: a) measuring the baseline of the resting tissue of a user; b) transmitting light energy pulses into a body tissue of the user which interrogates the tissue with low-energy radiation allowing the glucose measurement up to a few mm under the skin; c) detecting the vibration of body tissue resulting from the light energy pulses being transmitted, wherein the vibrations generate an acoustic signal; and d) analyzing the acoustic signal using at least one algorithm to determine the difference between the baseline and final level of vibration, wherein the algorithm interprets the level of vibrations into the amount of blood glucose (Jyoti Y et al., "Near-infrared LED based Non-invasive Blood Glucose Sensor", 2014 International Conference on Signal Processing and Integrated Networks (SPIN), IEEE, pp. 591-4).

Referring now to the drawings, and specifically to FIG. 1, a cross sectional view of a ring type device of the present invention. The ring 10 has embedded in the structure one or more optoelectronic devices such as infrared LEDs 20 that emit IR radiation between 700 and 1600 nanometers. In a preferred embodiment the IR LED operates at 930 nanometers which is able to penetrate the skin to a depth of several millimeters. One or more LEDs can be used for sampling blood flow dynamics through the vessels including, but not limited to the veins, arteries and capillaries. An example of a viable artery for BGL analysis includes the palmer arteries palmer arteries in the finger to which the ring is attached. Since the palmer arteries are close to the skin surface reliable and consistent data can be generated to determine multiple health related biological signals such as heart pulse rate, oxygen levels and BGL. Also included in the ring 10 is a photo detector 30 that measures the IR LED 20 waveforms and amplitude. A ring that can be used in the present invention is manufactured by Oura Health®, Ltd (Oulu, Finland). In another embodiment, the IR LED is a pulse oximeter which can determine health related parameters selected from a group consisting of, but not limited to, oxygen saturation, heart rate, respiratory rate, heart rate variability and combinations thereof. In yet another embodiment, the ring can be replaced with a watch, wristband, implantable RFID, headphones, headbands, earrings, mask and combinations thereof. This alternative embodiment would allow for measurements at various locations of the body including, but not limited to, the ears, hands, fingers, arm, forearm, check and combinations thereof.

Figure 2:
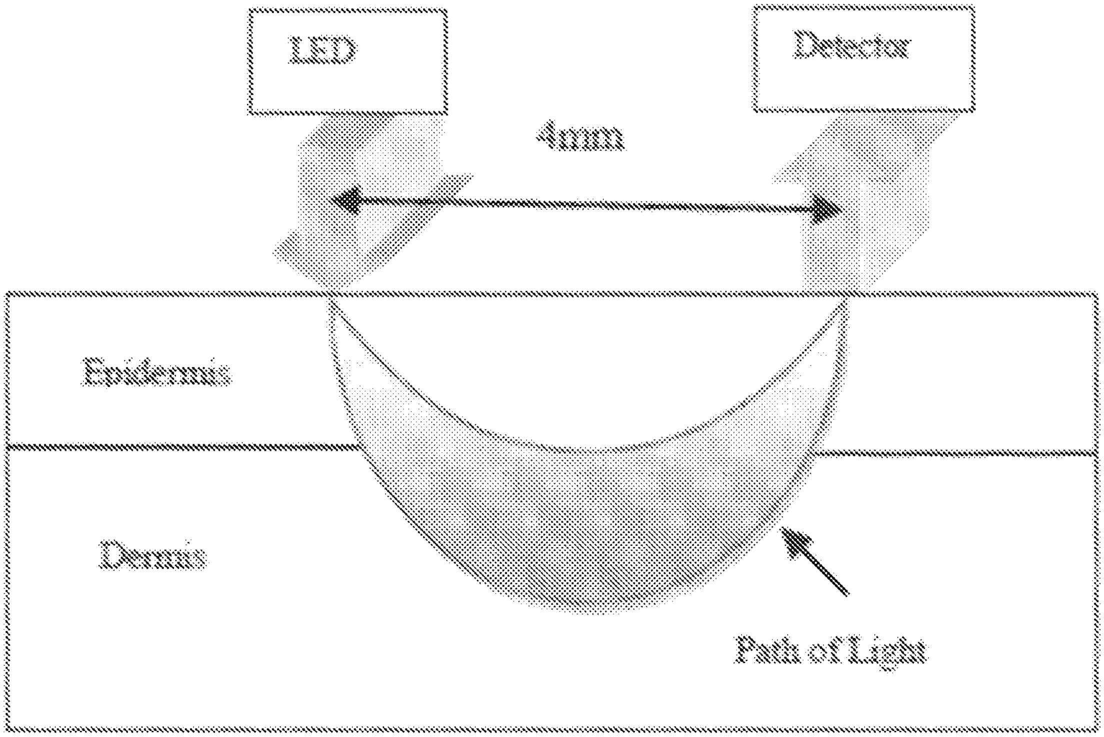
FIG. 2, shows the light path followed through the skin as generated by the ring and detected in the present invention.

FIG. 2., depicts a diagram of how IR LED light 20 penetrates the skin of an end user and is subsequently detected by a photodiode 30 of the ring 10. The distance from the IR LED 20 to the photodiode 30 labeled detector, can range from 0.1 to 5 millimeters with 1-2 millimeters being preferred. One of more LED waveforms can be measured, and the sampling rate can vary from 10 to 1000 samples per second with 200-300 being preferred. As the radiation interacts with biological tissue, it is attenuated by absorption as well as scattering. The attenuation of light can be described by light transport the provided theory:

$$I=I_l\theta^{ff}eff^{L}(i$$

In equation (1) I is the reflected light intensity, $I_o$ is the incident light intensity, L is the optical path-length in tissue, and the term $u_{eff}L$ is defined in equation (2) in terms of absorption coefficient up and reduced scattering coefficient $u_S'$ $$u_{eff}=[3u_a(u_a+u'_s)]^{1/2} \tag{2}$$

$$u_a=2.303eCcm-1 \tag{3}$$

Equation (3) shows relation of absorption coefficient up to the tissue chromophore concentration (C), where e is molar extinction coefficient. Value of up changes with variation in glucose concentration.

$$U'_s=U_s \text{ is } [1-g] \tag{4}$$

Equation 4 shows the expression for reduced scattering coefficient where g is the anisotropy factor and $u_s$ is scattering coefficient. Variation in glucose concentration affects the intensity of light scattered from the tissue.

By utilizing the aforementioned theory and mathematics, it is then possible to determine BGL levels from the data generated by the ring 10 of the present invention.

The infrared LEDs of the ring access blood volume pulse (BVP) directly from the palmar arteries of the finger, with similar technology as, for example, the pulse oximeters used in hospitals. The light sensor of the ring can capture 250 samples per second for a constant flow of reliable data. The ring detects the pulse waveform and amplitude variation, and exact time between heartbeats, i.e., inter-beat interval (IBI). From these, it derives the wearer's heart rate, respiratory rate, and heart rate variability (HIIV), as well as other health related parameters, such as BGL, can be determined with subsequent machine learning algorithms and subsequent data processing utilizing the aforementioned equations. In another embodiment, the device can be selected from a group consisting of, but not limited to, a watch, wristband, implantable RFID devices, headphones, headbands, earrings and combinations thereof.

Figure 3:
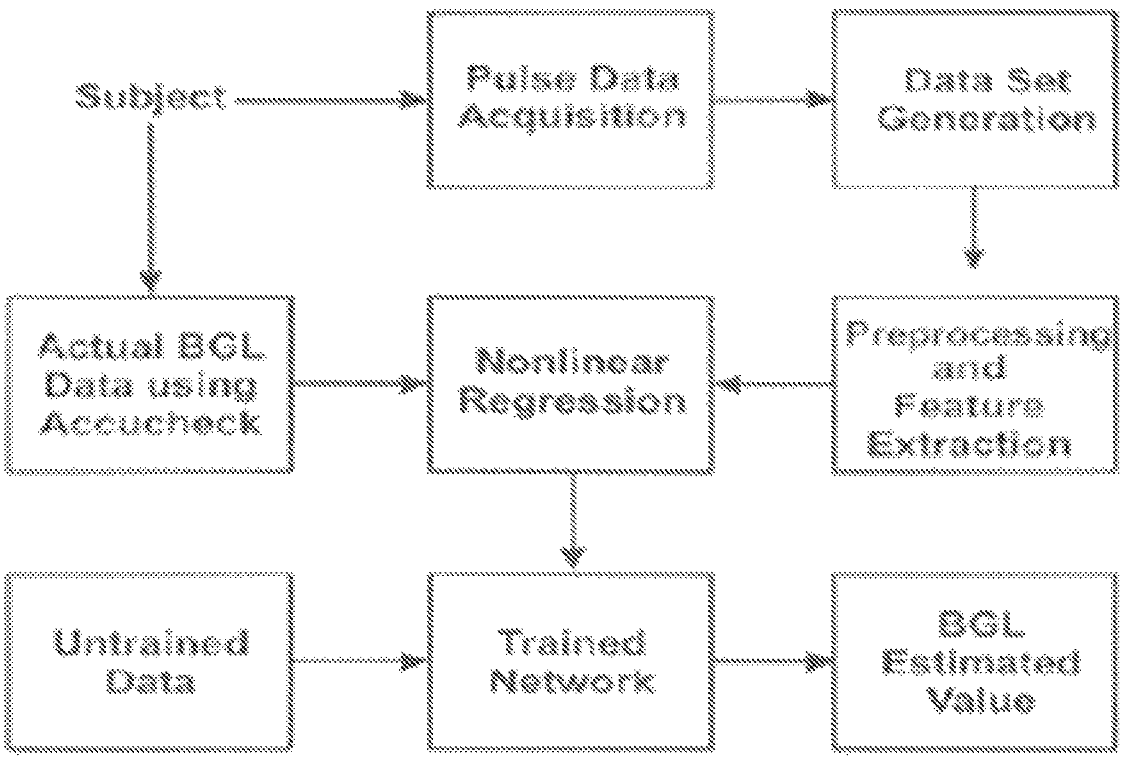
FIG. 3, shows a block flow diagram of a machine learning algorithm process utilized in the present invention.

FIG. 3., shows one example of a block diagram of how a machine learning algorithm that can be deployed to take captured data front the ring 10 and with analysis of large data sets over time of diabetic and non-diabetic subjects to calculate real time blood glucose levels non-invasively. It starts with a subject that wears a ring 10 to collect data on a 24/7 basis. During the data collection period the subject periodically captures either blood draw test data by using standard glucose meter kits, such as the Accu-Chek® brand blood glucose monitoring kits (Roche Diabetes Care GmbH, Mannheim, Germany), or alternatively, the Dexcom G6® Continuous Glucose Monitoring (CGM) System, an invasive continuous monitoring product (Dexcom, Inc, San Diego, CA). Data set generation from the ring 10 is pre-processed and relevant information is extracted to calculate the BGL of the wearer. The ring 10 data is then correlated with actual invasive data with a nonlinear regression or equivalent mathematical technique. The trained network after numerous machine learning iterations or processing by neural networks as taught by Habbu et al. (Habbu S et al., (2019), Sādhanā, 44(135):1-14) can then take untrained data from any subject and calculate the wearer's BGL with high accuracy using a noninvasive ring 10. As the network of users increases the data set generation and machine learning BGL calculations increases, the system learns exponentially which will increase accuracy of BGL prediction to over 90% and most likely great than 95%. The BGL results can be sent and displayed to a mobile device such as a smart phone, tablet or to the cloud for subsequent storage, accessibility and further analysis.

In the preferred embodiment, the wearable wireless non-invasive system can be manufactured through a process selected from a group consisting of, but not limited to, one-shot molding, two-shot molding, or multi-material injection molding and combinations thereof. This process can be completed through technique consisting of, but not limited to ejection molding, 3D printing, injection molding, thermoforming, compression molding, rotational molding, vacuum casting, resin casting, and combinations thereof. In addition, in the preferred embodiment, the wearable wireless non-invasive system is manufactured from a material selected from a group consisting of polymers, metals, non-metals, metalloids and combinations thereof.

In the preferred embodiment, the wearable wireless non-invasive system can be used to determine blood glucose levels (BGL) and said use can be applied to the healthcare industry, education industry, retail industry, business industry and combinations thereof.

The above discussion is meant to be illustrative of the principle and various embodiments of the present invention. Numerous variations, combinations and modifications will become apparent to those skilled in the art once the above disclosure is fully appreciated such as using big data analytics, genetic algorithms, various layered neural networks. In addition, other wearables such as a watch, wristband or an implantable RFID can be used and BGL artery measurements from other parts of the body such as the wrist, and ear may be acceptable. It is intended that the following claims be interpreted to embrace all such variations and modifications.

I claim:

1. A wearable, non-invasive system that measures in real-time the blood glucose levels in a patient diagnosed with diabetes comprising:

an ultrasonic transducer;

an optoelectronic device comprising an infrared light emitting diode-enabled device (IR LED) that emits energy pulses that penetrate the skin of the patient and into body tissue;

a photodiode labeled detector designed to take measurements from one or more blood vessels; and a microcontroller;

wherein the ultrasonic transducer detects vibration of body tissue and transmits an acoustic signal to the microcontroller that uses a machine learning algorithm that determines the difference between the baseline and final glucose levels with an accuracy exceeding 90%;

wherein the distance from the infrared light emitting diode-enabled (IR LED) device to the photodiode labeled detector ranges from 0.1 to 5 millimeters, preferably between 1 to 2 millimeters.

2. The wearable system according to claim 1, wherein said photodiode labeled detector designed to take measurements from one or more blood vessels, wherein said blood vessels are selected from the group consisting of veins, arteries, capillaries and combinations thereof.

3. The wearable system according to claim 2, wherein said one or more blood vessels are palmer arteries.

4. The wearable system according to claim 1, wherein the photodiode labeled detector measures the infrared light emitting diode waveforms and amplitude.

5. The wearable wireless non-invasive system according to claim 1, wherein said infrared light emitting diode-enabled (IR LED) device measures the wearer's blood flow using photoplethysmography (PPG).

6. The wearable wireless non-invasive system according to claim 1, wherein said measurements are recorded at the ears, hands, fingers, arm, forearm, cheek and combinations thereof of the patient.

7. The wearable wireless non-invasive system according to claim 1, wherein said wireless non-invasive system is embedded into a wearable ring, watch, wristband, implantable radio-frequency identification (RFID) device, headphones, headbands, earrings, mask or any combinations thereof.

8. The wearable wireless non-invasive system according to claim 7, wherein said wireless non-invasive system is embedded into the wearable ring, wherein said ring is manufactured using a manufacturing process selected from the group consisting of one-shot molding, two-shot molding, multi-material injection molding and combinations thereof.

9. The wearable wireless non-invasive system according to claim 1, wherein said wireless non-invasive system is embedded into a wearable ring, wherein said ring is manufactured using a manufacturing process selected from the group consisting of ejection molding, 3D printing, injection molding, thermoforming, compression molding, rotational molding, vacuum casting, resin casting and combinations thereof.

10. The wearable wireless non-invasive system according to claim 1, wherein said system is manufactured from a material selected from a group consisting of polymers, metals, nonmetals, metalloids and combinations thereof.

11. The wearable wireless non-invasive system according to claim 1, wherein said optoelectronic device emits IR radiation between 700 and 1600 nanometers, provided said IR radiation penetrates the wearer's skin to a depth of several millimeters.

12. The wearable wireless non-invasive system according to claim 1, wherein said optoelectronic device emits IR radiation of 930 nanometers at a depth of several millimeters.

* * * * *